United States Patent [19]
Lubek et al.

[11] Patent Number: 6,116,098
[45] Date of Patent: Sep. 12, 2000

[54] DEVICE FOR SAMPLING AND/OR INJECTING FLUIDS LIABLE TO EVOLVE ACCORDING TO A REVERSIBLE REACTION

[75] Inventors: Albert Lubek, La Celle Saint Cloud; Fabrice Lecomte; Etienne Lebas, both of Rueil Malmaison, all of France

[73] Assignee: Institut Francais du Petrole, Cedex, France

[21] Appl. No.: 09/104,165

[22] Filed: Jun. 25, 1998

[30] Foreign Application Priority Data

Jun. 25, 1997 [FR] France .................................. 97 08081

[51] Int. Cl.[7] ...................................................... G01N 1/14
[52] U.S. Cl. ..................................... 73/863.83; 73/863.11; 73/864.16; 73/864.22; 141/311 R; 422/100
[58] Field of Search ............................ 73/864.62, 863.83, 73/863.84, 864.16, 864.22, 863.11, 863.01, 863.02, 863.03; 422/100, 102; 141/311 R

[56] References Cited

U.S. PATENT DOCUMENTS

| | | | |
|---|---|---|---|
| 4,038,030 | 7/1977 | Albright et al. | 436/165 |
| 4,634,680 | 1/1987 | Kingsley | 436/178 |
| 4,919,893 | 4/1990 | Bandurski et al. | 422/78 |
| 5,088,335 | 2/1992 | LaFreniere et al. | 73/864.62 |
| 5,152,678 | 10/1992 | Zeck | 417/401 |
| 5,275,786 | 1/1994 | Soleta et al. | 422/81 |
| 5,554,811 | 9/1996 | Rokugawa et al. | 73/864.34 |

FOREIGN PATENT DOCUMENTS

| | | |
|---|---|---|
| 367899 | 5/1990 | European Pat. Off. . |
| 0455333 | 11/1991 | European Pat. Off. . |
| 4030729 | 4/1992 | Germany . |
| 83659 | 4/1987 | Japan . |
| 232412 | 9/1990 | Japan . |
| 9005291 | 5/1990 | WIPO . |
| 9206363 | 4/1992 | WIPO . |

*Primary Examiner*—Thomas P. Noland
*Attorney, Agent, or Firm*—Antonelli, Terry, Stout & Kraus, LLP

[57] ABSTRACT

The invention is a device for sampling and/or injecting a fluid which evolves according to a reversible reaction, that enables the fluid to be restored to its initial state. The device inside a fluid sampling enclosure produces a counterpressure value necessary for restoring the fluid to its initial state without causing a change in its composition.

38 Claims, 2 Drawing Sheets

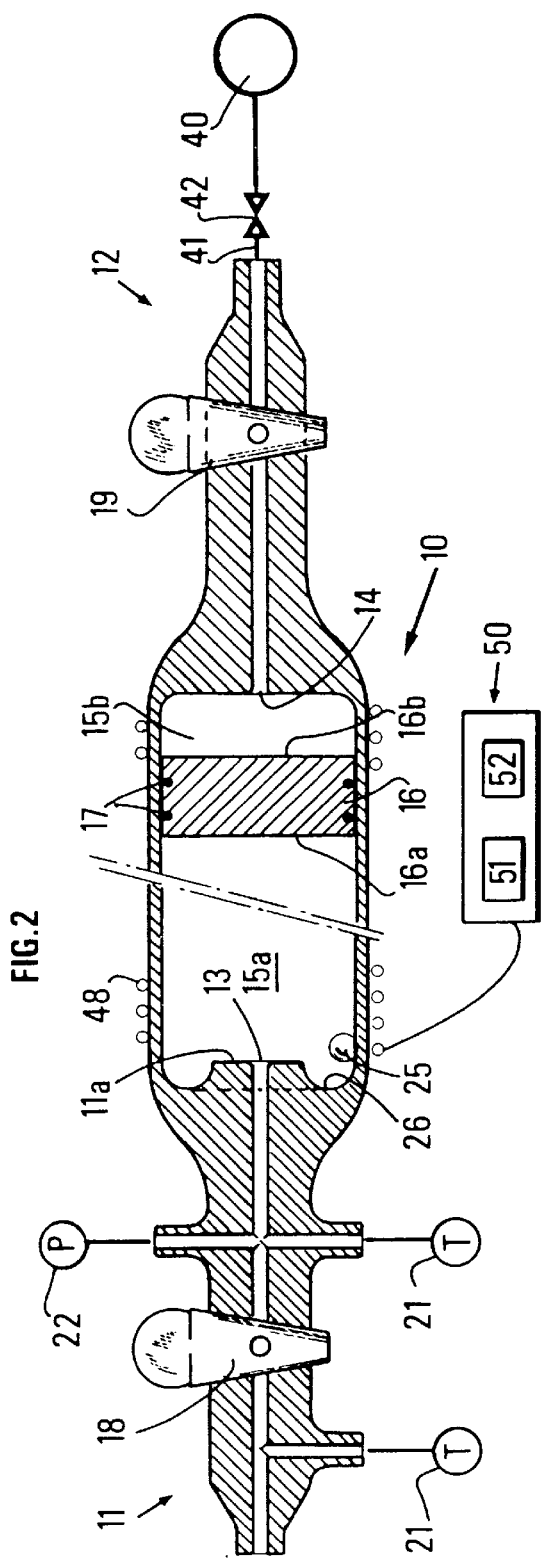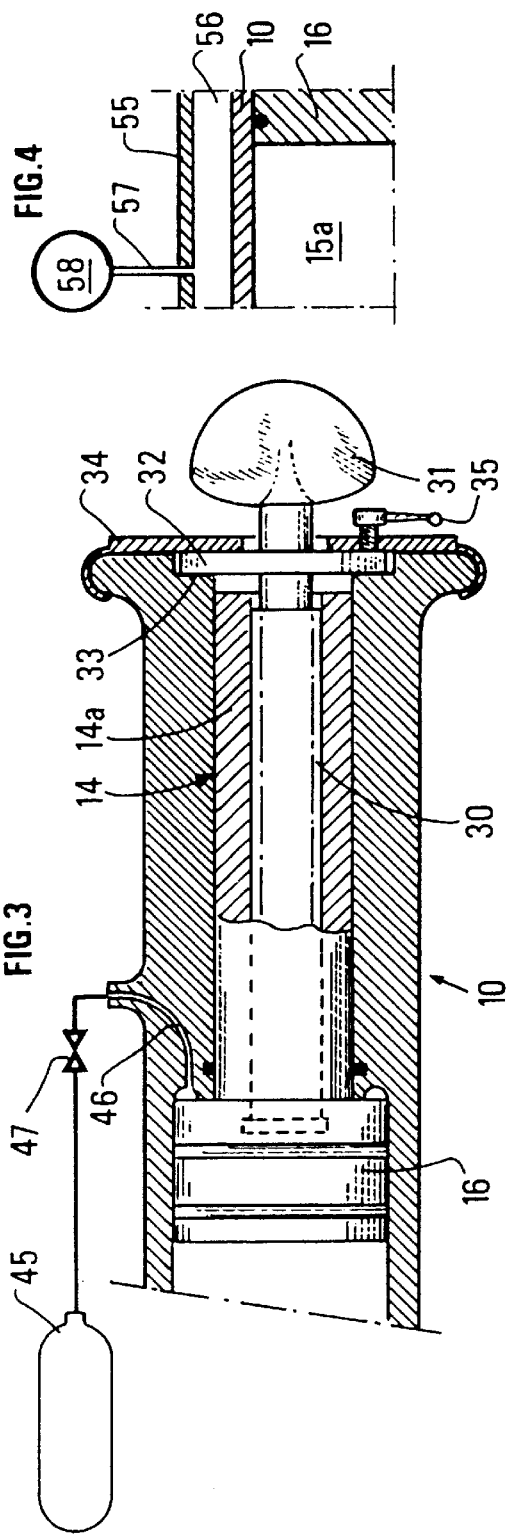

DEVICE FOR SAMPLING AND/OR INJECTING FLUIDS LIABLE TO EVOLVE ACCORDING TO A REVERSIBLE REACTION

BACKGROUND OF THE INVENTION

1. Field of the Invention

The present invention relates to a device for sampling and/or injecting fluids whose composition is liable to evolve reversibly under the effect of a change for example, in a thermodynamic parameter.

Various devices for sampling a fluid under analysis are described in the prior art.

2. Description of the Prior Art

One example of a device according to the prior art is shown in FIGS. 1, 1A, and 1B. It enables a sample of gaseous, liquid, or multiphase fluid composed of several phases of different natures to be sampled from a treatment unit so that a chemical or physicochemical analysis of this sample can be performed. The sampling device comprises a chamber 1 initially filled with liquid mercury, the mercury being expelled through orifice 2 when the chamber is filled with liquid entering through orifice 3 (FIG. 1A).

When sampling is complete (FIG. 1B), orifices 2 and 3 are closed by valves or stopcocks 4, and the device containing the sample is transported to the analysis device. During this transportation, the thermodynamic conditions may change, and it becomes necessary to restore the fluid sample to a state substantially identical to its initial state to obtain a representative analysis. For example, if the sample has at least partially vaporeeed during the sampling operation, an attempt is made to restore the sample to an essentially liquid state corresponding essentially to its original state by injecting a given quantity of mercury through orifice 3, opening 2 being closed. The phase that vaporizes is then recompressed and is converted into a liquid phase.

It is also possible to monitor and restore the temperature conditions when the rheological behavior of the fluid sample is to be studied, for example by placing this device in an oven.

While such a device does allow the fluid to be kept in or restored to its initial state to overcome the sampling conditions and thus obtain representative analysis results, it has nonetheless the drawback of using mercury which is a harmful product which, when placed in direct contact with the fluid sample, can interact with the latter and alter its nature.

Another procedure described in the prior art consists of analyzing the fluid without restoring it to its initial state by analyzing the liquid and vapor phases separately, then correcting the results obtained by calculating the liquid-vapor balance, taking into account the compositions of each of the phases to determine the state of the sample corresponding to given sampling conditions.

Such a method is effective but may be complex and slow.

SUMMARY OF THE INVENTION

The present invention overcomes the disadvantages of the prior art devices. It relates to a device enabling a fluid that may change state when acted upon by a change in an outside parameter, such as a change in a thermodynamic parameter, to be sampled and/or injected, and restores the sampled fluid to its initial state without modifying the nature, particularly the composition and chemical characteristics of the fluid.

The device according to the invention is very appropriate for sampling a fluid that is initially in a liquid state and, under the effect of a change in pressure, will vaporize at least in part.

The device according to the invention keeps fluid in or restores the fluid to a given state, for example, the state in which the fluid was initially before a sampling and/or injection step.

In the context of the present invention, the term "reversible reaction" designates a reaction during which a shift in an equilibrium, for example, the thermodynamic equilibrium of a reaction between the components of a fluid, and causes no definitive change in the composition or the nature of the fluid.

The initial state of the fluid can be determined, for example, as a function of the respective nature and quantities of the components of the fluid. The initial state can be defined with respect to the state of the fluid in a treatment unit such as a natural gas liquefaction unit, or any other location containing a fluid to be analyzed.

The present invention relates to a device for sampling and/or injecting a fluid of a given composition and nature, the fluid being subject to a reversible reaction. In particular, the device enables the fluid to be restored to a state substantially identical to the initial state thereof without the nature of the fluid changing, the device comprising an enclosure comprising a cavity and at least two ends, each of the ends being equipped with at least one opening for passage of the fluid.

The device comprises means disposed inside the enclosure, the means enabling the fluid sampled or injected to be restored to the initial state thereof without causing a change in the nature of the fluid.

According to one embodiment, the means for restoring the fluid to a given state are designed to apply to the sampled and/or injected fluid the counterpressure necessary to restore an essentially liquid fluid, at least partially vaporized due to a change in an external parameter, to a substantially liquid state.

The means for applying a counterpressure may comprise a plunger and a pressurized gas reservoir.

The value of the pressure applied to the sampled and/or injected fluid is between atmospheric pressure and 30 MPa, preferably between atmospheric pressure and 15 MPa.

The openings can be provided with means providing a controlled communication between cavity and the outside, the means being connected to manual and/or pneumatic and/or electrical control devices.

The device comprises for example auxiliary temperature control means for maintaining and/or adjusting the temperature, the temperature value being between −170° C. and +200° C., preferably between −30° C. and +150° C.

The temperature control means can be a Peltier-type device and/or comprise an electrical heating device located at the sampling system and/or comprise means for containing a thermostatically controlled fluid.

The device can comprise temperature- and/or pressure-controlling means.

According to one embodiment, the device comprises means for connecting the various temperature-holding and/or pressure-restoring elements to an external energy source such as rechargeable electrical batteries or batteries located in automobiles.

A particularly suitable application of the device is sampling and/or injecting a fluid such as a liquefied gas from a liquefaction unit and re-injecting thereof into an analysis device.

By comparison to the prior art, the device according to the invention has the following advantages in particular:

the use of fluids that could react or contaminate the analysis fluid when in contact therewith is avoided, by comparison to the classical device, the sampling cylinder does not use mercury or another harmful fluid, which is an undeniable advantage from the standpoint of contamination and poisoning hazards incurred when handling;

the device is particularly suited for sampling a fluid from a low-temperature process with the aforementioned advantages.

A cavity can also be created from a double jacket extending over at least the length of the cavity body or over the total body, which is provided with one or more openings for filling the space thus formed with a heat-conducting fluid.

BRIEF DESCRIPTION OF THE DRAWINGS

Other advantages and characteristics of the present invention will emerge from reading the description provided hereinbelow as embodiment examples, in the framework of nonlimiting applications, with reference to the attached drawings wherein:

FIG. 2 shows an embodiment of the sampling and/or injection device according to the invention for restoring a fluid that may have, for example, evolved under the effect of a change in one or more thermodynamic parameters, and FIG. 3 shows schematically a detail of the opening of the device equipped with means for producing the counterpressure.

FIG. 4 shows an embodiment of a temperature control for the embodiment of the invention of FIG. 2.

DETAILED DESCRIPTION OF THE INVENTION

Figure 1:
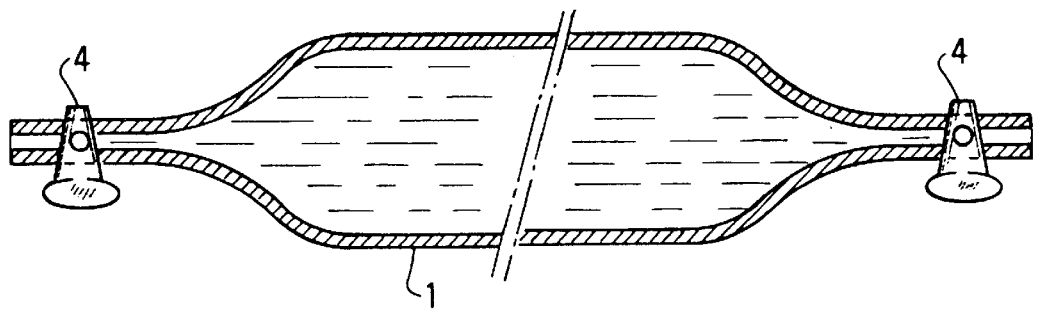
FIGS. 1, 1A, and 1B show a sampling device according to the prior art.
Figure 1A:
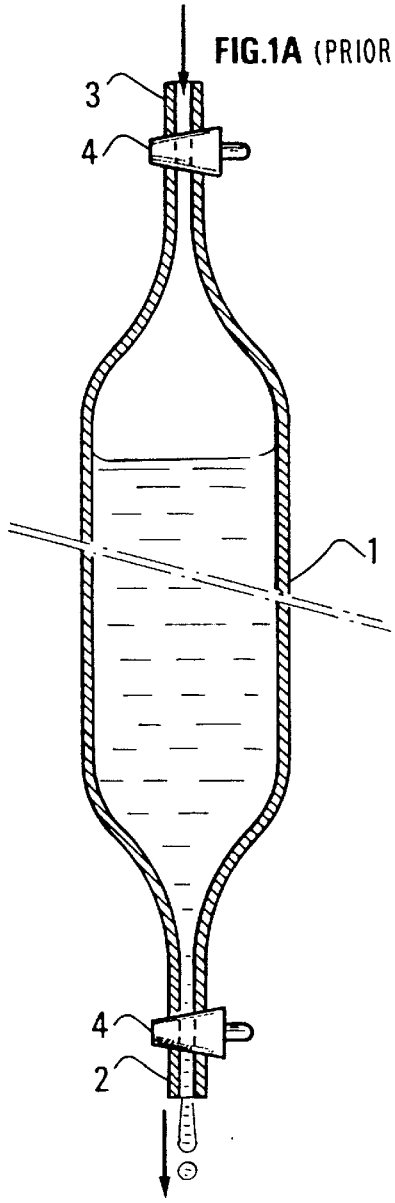
Figure 1B:
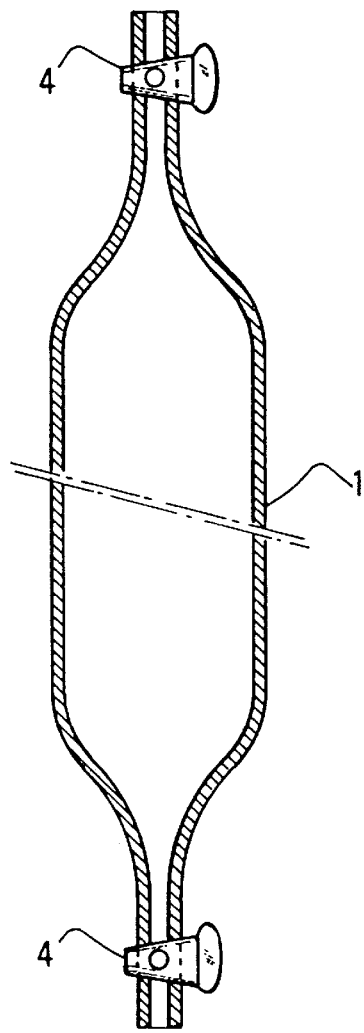

For better understanding of the characteristics of the sampling device according to the invention, FIG. 2 shows a sampling device designed to sample and/or inject a fluid such as a liquefied gas, the device comprising a plunger for restoring the liquefied gas at least partially vaporized during the sampling stage to an essentially liquid state. The fluid restored to the original state will then be injected into an analysis device.

The device shown in FIG. 2 comprises a body or enclosure 10 having two ends 11, 12 and a cavity 15, numbered (15a, 15b) in the figure. Each of the ends 11, 12 has at least one opening 13, 14 for passage of fluid, which are respectively fitted with closing and/or a regulating means 18, 19 such as stopcocks which can serve to regulate or control the flow of fluids entering or leaving cavity 15. These stopcocks are connected for example to manual, pneumatic, or electrical control devices.

Inside cavity 15 are means such as a plunger 16 with O-rings 17, so that plunger 16 defines two chambers 15a, 15b of variable volume. Movement of plunger 16 in cavity 15 enables an equilibrium that may evolve under the effect of an external parameter such as temperature and/or pressure to be reestablished.

The device is also fitted with temperature and pressure sensors numbered 21 and 22 respectively which can be distributed throughout the device.

Plunger 16 is designed so that the sampling device preferably operates in a pressure range preferably between atmospheric pressure and 30 MPa and preferably between atmospheric pressure and 15 MPa.

The device can include means for homogenizing the fluid inside the cavity, which may be in the form of a mixing ball 25 (FIG. 2). In this case, the wall of the cavity at end 11 has at least one recess 26 designed to receive the mixing ball when the plunger is retracted and is applied to this wall.

The device can also have means 48 for heating and/or holding at a given temperature, which may be distributed through the entire device, particularly at the cavity of the enclosure. A heating resistor 48 for example or a Peltier effect device is used. It is also possible to use a heating means having a double jacket containing a heat-conducting fluid, as shown schematically in FIG. 4.

A control box 50 containing a battery 51 and a temperature control means 52 for automatically controlling and regulating the temperature of the fluid sample at a setpoint established by the user can be connected to the sampling device. The temperature range in which one operates is for example between −170° C. and 200° C., and preferably between −30° C. and 150° C.

The device can also have a battery built into the cylinder body, omitted from the figure in order to simplify the figure, with a life of several hours of at least four hours. The device can then be equipped with an electrical plug so that it can be connected to a power source.

Movement of plunger 16 in the cavity enables the filling and discharge (sampling and injection) operations to be performed and the fluid to be kept in and/or restored to a given state.

This movement can be effected in various ways, of which some examples are provided below for illustrative and nonlimiting purposes.

The device can be equipped with a manual displacement, not shown, which act simply translationally, which are connected to the plunger and disposed in passage 14 for example.

FIG. 3 shows schematically another embodiment that uses a system of threaded rods to move the plunger.

One or more threaded rods are disposed at opening 14. This opening can be cylindrical in shape and translationally guide a rod 14a that is translationally integral with plunger 16. In FIG. 3, rod 14a is tapped to cooperate with a threaded rod 30. This threaded rod 30 is translationally immobilized by a stop 32 while retaining freedom of rotation. The rotational movement of rod 30, which is provided by a knob 31 for example, has the effect of displacing plunger 16 translationally by means of rod 14a.

Stop 32 is held with respect to enclosure 10 by a shoulder 33 and a cover 34. A lock 35 enables the plunger to be kept in a given position inside cavity 15 to maintain a given pressure.

The plunger is displaced until the counterpressure necessary and sufficient for keeping a liquefied gas in or restoring it to a liquid state corresponding to its state in the liquefaction unit is obtained.

If the sampled fluids are at a pressure greater than atmospheric, rod 14a can simply press on face 16b of plunger 16 to obtain the desired counterpressure effect.

Another procedure consists of moving piston 16 using a fluid under pressure, for example a compressed gas from an external source 40.

For this purpose, a first embodiment shown in FIG. 2 consists of connecting compressed gas source 40 directly by a pipe 41 to passage 14. Pipe 41 can be equipped with a valve 42 for regulating the quantity of injected gas.

The compressed gas is sent through pipe 41 to chamber 15b. It applies a pressure to face 16b, causing plunger 16 to move until the vaporized gas is liquefied. The counterpressure value is measured for example with pressure sensor 22 (FIG. 2) or a pressure gauge, with the quantity of injected gas being regulatable for example by valve 42 or any other appropriate device with which the pipe is fitted.

Another variant using a fluid under pressure is shown schematically in FIG. 3 and comprises an external source 45 connected by a pipe 46 passing through the wall of enclosure 10 to plunger 16. Pipe 46 can also be equipped with a valve 47 regulating the compressed gas flowrate.

When applied to sampling a liquefied gas from a liquefaction unit, these operations comprise for example the following steps:

- With stopcock 18 closed and stopcock 19 open, a neutral gas under pressure, for example nitrogen, is introduced into variable volume chamber 15 through opening 14. At the end of this first step, plunger 16 is pressed against wall 11a, and when a mixing ball is in the cavity, it is received in recess 26.
- Stopcock 18 is connected to the liquefaction unit by appropriate means, for example a sampling tap, stopcock 18 being in the closed state and stopcock 19 being open to atmosphere.
- With the aid of appropriate means, which can be attached to the device according to the invention, the liquefied gas to be sampled upstream of stopcock 18 is expelled.
- The values of the thermodynamic parameters, the temperature value Ti and the pressure value Pi, in the liquefaction unit are noted and stored for example in control box 50.
- Stopcock 18 is then opened. The liquefied gas sample fills chamber 15a, while plunger 16 is retracted to the opposite end of cavity 15.
- After the pressure and/or temperature values have stabilized, these values Pf and Tf are determined.
- Values Pf and Tf and values Pi and Ti determined previously or established initially are used to deduce the evolution or change in state of the liquefied gas. Thus it is possible to determine the degree of vaporization of the liquefied gas sample and deduce the counterpressure value to be applied to restore this gas to an essentially liquid state corresponding to its initial state in the liquefaction unit.

To produce the counterpressure, a quantity of pressurized gas is injected into pipe 46, and controlled with valve 47. This quantity can be determined by the control box as a function of the plunger movement necessary to liquefy the vapored part of the gas. The movement can be accomplished according to one of the means described above.

After these steps, the liquefied gas is in a state essentially identical to its initial state in the liquefaction unit and it can be analyzed in the absence of interfering phenomena.

FIG. 4 shows schematically the embodiment described above where temperature holding and/or raising is/are produced by a heat-conducting fluid contained in a jacket surrounding the cavity.

Enclosure 10 comprises a jacket 55 disposed around cavity 15a and forming a gap 56 with respect thereto. Gap 56 can be connected by a pipe 57 to an external source 58 containing a heat-conducting fluid.

Instead of using nitrogen, it is possible to fill the cylinder by creating a vacuum in variable volume chamber 15a. Nonetheless, movement of the piston is less controlled than when neutral gas is injected under pressure as described above.

The principle of the invention is shown by the following two examples, which are not limiting.

EXAMPLE 1

The goal is to sample and analyze the composition of a liquid initially at a temperature of −25° C. and a pressure of 3 MPa.

The liquid sampled has for example the following composition expressed in molar fractions:

| | |
|---|---|
| water | 0.005 |
| methanol | 0.931 |
| $CO_2$ | 0.010 |
| $H_2S$ | 0.008 |
| methane | 0.031 |
| ethane | 0.002 |
| propane | 0.013 |

When this liquid mixture is removed at a temperature of 20° C. and atmospheric pressure, the equilibrium state of this liquid mixture is disturbed and at least part of it is vaporized. The mixture is then in a two-phase form comprising a liquid phase and a vapor phase.

To restore the initial equilibrium and restore the mixture to an essentially liquid form, stopcock 18 is closed and, following the steps listed above, a counterpressure of approximately 4 MPa is produced, while keeping the temperature at approximately 20° C.

Preferably, a safety pressure value of approximately 4.5 MPa is applied.

Now that the mixture is once again in a state substantially identical to its initial state, it can be injected into a chromatograph for direct analysis.

While operating according to the prior art, the vapor phase, comprised mainly of methane and $CO_2$, and the liquid phase, comprised principally of methanol, would have had to be analyzed.

EXAMPLE 2

A liquid is sampled at a temperature of −17° C. and a pressure of 7.1 MPa. Composition (molar fractions):

| | |
|---|---|
| water | 0.204 |
| methanol | 0.674 |
| $CO_2$ | 0.075 |
| methane | 0.028 |
| ethane | 0.011 |
| propane | 0.008 |

At the temperature of 20° C. and atmospheric pressure, this mixture is in the form of two phases, namely a vapor phase and a liquid phase. In this example, the minimum pressure to be maintained in the cylinder for the mixture to remain liquid at a temperature of 20° C. is 9.6 MPa. A counterpressure of 100 MPa is then applied following the steps listed above.

When sampling is to be done at a temperature of approximately −10° C., a Peltier effect device for example can be used, located around the sampling cylinder, in order to keep the temperature value essentially stable.

To keep the temperature at approximately 100° C. for example, it is also possible to use a heating resistor built into the cavity for example or any other means leading to an identical result.

What is claimed is:

1. A device for sampling and/or injecting a fluid which evolves in a reversible reaction, enabling the fluid to be restored to a state substantially identical to an initial state thereof without causing a change in the nature of the fluid, comprising:

an enclosure comprising a cavity and two ends, each of the ends being provided with at least one opening for passage of the fluid, a device disposed inside the enclosure which applies a counterpressure to the fluid which restores an essentially liquid fluid, at least partially vaporized due to a change in an external parameter, to a substantially liquid state without causing a change in a nature of the fluid.

2. A device according to claim 1, wherein the device which applies a counterpressure comprises a plunger and a pressurized gas reservoir.

3. A device according to claim 2, wherein a value of the pressure applied to the fluid is between atmospheric pressure and 30 MPa.

4. A device according to claim 3, wherein the pressure applied to the fluid is between atmospheric pressure and 15 MPa.

5. A device according to claim 4, wherein the openings are provided with means providing a controlled communication between the cavity and an outside of the cavity, the means being connected to at least one of manual, pneumatic or electrical control devices.

6. A device according to claim 5, further comprising:
a temperature control which performs at least one of maintaining or adjusting temperature in the cavity, to a temperature value between −170° C. and +200° C.

7. A device in accordance with claim 6 wherein:
the temperature value is between −30° C. and 150° C.

8. A device according to claim 4, further comprising:
a temperature control which performs at least one of maintaining or adjusting temperature in the cavity, to a temperature value between −170° C. and +200° C.

9. A device in accordance with claim 8 wherein:
the temperature is between −30° C. and 150° C.

10. A device according to claim 3 wherein the openings are provided with means providing a controlled communication between the cavity and an outside of the cavity, the means being connected to at least one of manual, pneumatic or electrical control devices.

11. A device according to claim 10, further comprising:
a temperature control which performs at least one of maintaining or adjusting temperature in the cavity, to a temperature value between −170° C. and +200° C.

12. A device in accordance with claim 11 wherein:
the temperature value is between −30° C. and 150° C.

13. A device according to claim 3, further comprising:
a temperature control which performs at least one of maintaining or adjusting temperature in the cavity, to a temperature value between −170° C. and +200° C.

14. A device in accordance with claim 13 wherein:
the temperature is between −30° C. and 150° C.

15. A device according to claim 2, wherein the openings are provided with means providing a controlled communication between the cavity and an outside of the cavity, the means being connected to at least one of manual, pneumatic or electrical control devices.

16. A device according to claim 15, further comprising:
a temperature control which performs at least one of maintaining or adjusting temperature in the cavity, to a temperature value between −170° C. and +200° C.

17. A device in accordance with claim 16 wherein:
the temperature is between −30° C. and 150° C.

18. A device according to claim 2, further comprising:
a temperature control which performs at least one of maintaining or adjusting temperature in the cavity, to a temperature value between −170° C. and +200° C.

19. A device in accordance with claim 18 wherein:
the temperature value is between −30° C. and 150° C.

20. A device according to claim 1, wherein a value of the pressure applied to the fluid is between atmospheric pressure and 30 MPa.

21. A device according to claim 20, wherein the pressure applied to the fluid is between atmospheric pressure and 15 MPa.

22. A device according to claim 21, wherein the openings are provided with means providing a controlled communication between the cavity and an outside of the cavity, the means being connected to at least one of manual, pneumatic or electrical control devices.

23. A device according to claim 22, further comprising:
a temperature control which performs at least one of maintaining or adjusting temperature in the cavity, to a temperature value between −170° C. and +200° C.

24. A device in accordance with claim 23 wherein:
the temperature value is between −30° C. and 150° C.

25. A device according to claim 21, further comprising:
a temperature control which performs at least one of maintaining or adjusting temperature in the cavity, to a temperature value between −170° C. and +200° C.

26. A device in accordance with claim 25 wherein:
the temperature is between −30° C. and 150° C.

27. A device according to claim 20, wherein the openings are provided with means providing a controlled communication between the cavity and an outside of the cavity, the means being connected to at least one of manual, pneumatic or electrical control devices.

28. A device according to claim 27, further comprising:
a temperature control which performs at least one of maintaining or adjusting temperature in the cavity, to a temperature value between −170° C. and +200° C.

29. A device in accordance with claim 28 wherein:
the temperature value is between −30° C. and 150° C.

30. A device according to claim 20, further comprising:
a temperature control which performs at least one of maintaining or adjusting temperature in the cavity, to a temperature value between −170° C. and +200° C.

31. A device in accordance with claim 30 wherein:
the temperature is between −30° C. and 150° C.

32. A device according to claim 1, wherein the openings are provided with means providing a controlled communication between the cavity and an outside of the cavity, the means being connected to at least one of manual, pneumatic or electrical control devices.

33. A device according to claim 32, further comprising:
a temperature control which performs at least one of maintaining or adjusting temperature in the cavity, to a temperature value between −170° C. and +200° C.

34. A device in accordance with claim 33 wherein:
the temperature is between −30° C. and 150° C.

35. A device according to claim 33, wherein the temperature control is one of a Peltier-type device, an electrical heating device located in or of a sampling system and a receiver of a thermostatically controlled fluid which is thermally coupled to the cavity.

36. A device according to claim 1, further comprising:
a temperature control which performs at least one of maintaining or adjusting temperature in the cavity, to a temperature value between −170° C. and +200° C.

37. A device in accordance with claim 36 wherein:
the temperature value is between −30° C. and 150° C.

38. A process comprising:
sampling and/or injecting a fluid from a liquefaction unit with the device in accordance with claim 1.

* * * * *